(12) United States Patent
Capocchi

(10) Patent No.: US 7,700,579 B2
(45) Date of Patent: Apr. 20, 2010

(54) PROCESS FOR THE PREPARATION OF PIROXICAM: B-CYCLODEXTRIN INCLUSION COMPOUNDS

(75) Inventor: Andrea Capocchi, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 182 days.

(21) Appl. No.: 10/516,945

(22) PCT Filed: Jun. 12, 2003

(86) PCT No.: PCT/EP03/06142

§ 371 (c)(1),
(2), (4) Date: Aug. 23, 2005

(87) PCT Pub. No.: WO03/105906

PCT Pub. Date: Dec. 24, 2003

(65) Prior Publication Data

US 2006/0135473 A1 Jun. 22, 2006

(30) Foreign Application Priority Data

Jun. 17, 2002 (EP) .................................. 02013251

(51) Int. Cl.
*A61K 31/724* (2006.01)
*A61K 31/715* (2006.01)
*C08B 37/16* (2006.01)

(52) U.S. Cl. ........................ 514/58; 514/54; 536/103; 536/124

(58) Field of Classification Search .................... 514/54, 514/58; 536/103, 124
See application file for complete search history.

(56) References Cited

FOREIGN PATENT DOCUMENTS

| EP | 0 153 998 | | 9/1985 |
|----|-----------|---|--------|
| EP | 0153998   | * | 9/1985 |
| EP | 0 295 476 | | 12/1988 |
| WO | 91/13100  | | 9/1991 |
| WO | 95/28965  | | 11/1995 |

OTHER PUBLICATIONS

Acerbi, D. et al: "Biopharmaceutical optimisation of. beta.-cyclodextrin inclusion compounds." Drug Investigation, 2(Suppl. 4) pp. 29-36, 1990.

Nagarsenker, Mangal S. et al: "Influence of hydroxypropyl. beta.-cyclodextrin on dissolution of piroxicam and on irritation to stomach of rats upon oral administration" Indian Journal of Pharmaceutical Sciences, vol. 59, No. 4, pp. 174-180, 1997.

* cited by examiner

*Primary Examiner*—Shaojia Anna Jiang
*Assistant Examiner*—Michael C Henry
(74) *Attorney, Agent, or Firm*—Oblon, Spivak, McClelland, Maier & Neustadt, L.L.P.

(57) ABSTRACT

The present invention relates to a process for the preparation of inclusion compounds of piroxicam with β-cyclodextrin. More particularly, according to the process of the invention, the aqueous solution of two components is subjected, before drying, to a freezing process at very high rate. The resulting products have physico-chemical characteristics as well as technological and biopharmaceutical properties which are advantageous compared with those obtained according to the prior art processes. The resulting products are suitable for preparing pharmaceutical compositions for the oral administration.

12 Claims, 2 Drawing Sheets

PROCESS FOR THE PREPARATION OF PIROXICAM: B-CYCLODEXTRIN INCLUSION COMPOUNDS

Figure 1:
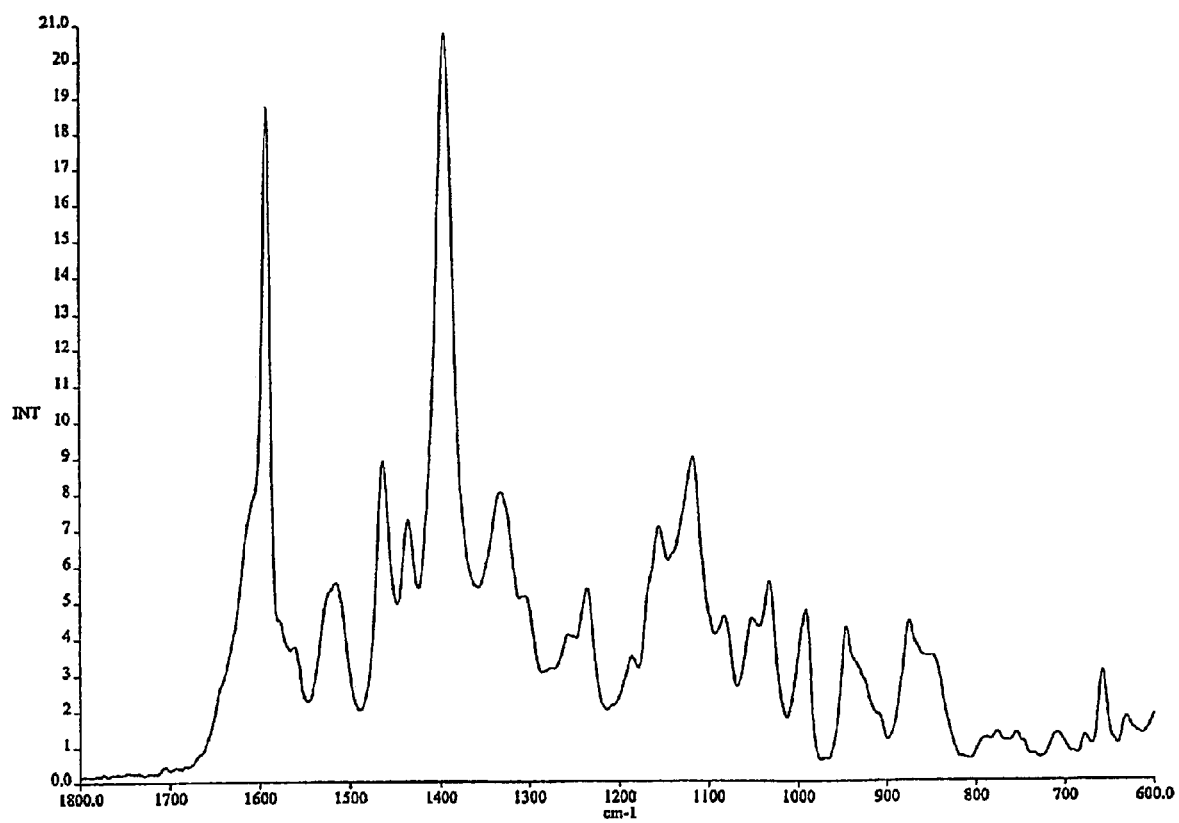

The present invention relates to a process for the preparation of inclusion compounds of piroxicam with β-cyclodextrin.

More particularly, according to the process of the invention, the aqueous solution of two components is subjected, before drying, to a freezing process at very high rate. The resulting products have physico-chemical characteristics as well as technological and biopharmaceutical properties which are advantageous compared with those obtained according to the prior art processes. The resulting products are suitable for preparing pharmaceutical compositions for the oral administration.

TECHNOLOGICAL BACKGROUND

Piroxicam is a compound belonging to the class of the Non Steroidal Anti-Inflammatory Drugs (NSAIDs) widely applied in rheumatoid arthritis, osteoarthritis, acute pain in musculoskeletal disorders, post-operative and post-traumatic pain and dysmenorrhoea.

Piroxicam is poorly soluble in water (0.003% at pH 5, 37° C.) and exhibits a low surface wettability (water contact angle 76°) and a high crystal lattice as demonstrated by its melting point (198-200° C.).

Since said molecule exhibits good membrane permeation characteristics, its low solubility is responsible for the slow dissolution rate in the gastro-intestinal fluids, which in turn results in slow absorption and delay in the onset of action.

Slow dissolution can also exacerbate local side effects associated to the drug (e.g. gastric irritation).

The handling of piroxicam is complicated due to its possible tautomeric switches and polymorphism. Said molecule indeed can exist in two polymorphic forms α and β, which have the same intramolecular structure EZE (I) but different intra- and intermolecular hydrogen bond interactions and in the pseudopolymorph which is the hydrate of the zwitter-ionic form ZZZ; one of the possible resonance forms of which is represented by formula (II) (Reck et al *Pharmazie* 1988, 43, 477; Bordner et al *Acta Crystallogr* 1984, C40, 989).

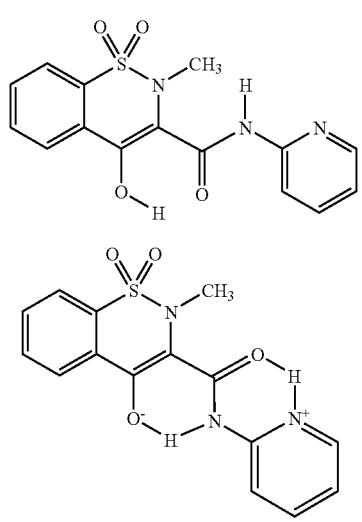

An efficient method for overcoming the problems related to the low solubility of piroxicam relies on the preparation of inclusion complexes with cyclodextrins as claimed in EP 153998. In the following disclosure, the terms complexes, inclusion complexes and inclusion compounds are used indifferently.

Cyclodextrins (CDs) are natural cyclic oligosaccharides having a torus-like macro-ring shape obtained by enzymatic degradation of starch. The three major cyclodextrins consist of 6(α), 7(β) or 8(γ) (1→4) D-glucopyranosidic units. Among them, βCD turned out to be the most useful for complexing piroxicam.

Pre-clinical and clinical studies have demonstrated that piroxicam:β-cyclodextrin inclusion compound (hereinafter indicated as PβCD) is characterized by an oral absorption pattern that is faster and more efficient than that of piroxicam alone (Deroubaix et al *Eur J Clin Pharmacol* 1995, 47, 531). In particular, the bioavailability of the active ingredient in terms of rate as well as of extent of absorption in the first two hours is greatly enhanced. As far as the stoichiometry is concerned, the inclusion complex with the molar ratio 1:2.5 was better compared with complexes with ratios of 1:1 or 1:4 (Acerbi, *Drug Invest* 1990, 2(4), 42).

The inclusion complex formation produces faster dissolution and absorption rate of piroxicam than any technological modification of the crystalline form known so far (Acerbi et al.: A pilot pharmacokinetic study after single oral administration of a sachet formulation of piroxicam:β-cyclodextrin inclusion complex versus a lyotablet formulation of plain piroxicam in healthy volunteers, *Poster presented at the 8th International Cyclodextrin Symposium*, Budapest, Mar. 30-Apr. 2, 1996; Wang D et al *J Clin Pharmacol* 2000, 40 (11), 1257-1266).

The more rapid onset of action makes PβCD particularly effective as analgesic, i.e. for the management of diseases such as dental pain, post-traumatic pain, headache and dysmenorrhoea.

The successful results achieved with the use of cyclodextrins rely on the fact that, through complexation, it is possible to obtain a stable amorphous structure; since the amorphous form has a larger surface area and its lattice energy is much less than in crystals, both wettability and aqueous solubility of piroxicam are increased. Amorphous piroxicam as such is, indeed, a metastable form which crystallises within few hours (Redenti et al *Int J Pharm* 1996, 129, 289).

Moreover, it has also been demonstrated by Raman studies that piroxicam, in the β-cyclodextrin inclusion compound, assumes a zwitter-ionic structure with positive and negative charges delocalized similar to that of the hydrate pseudopolymorph (II). This structure is stabilized due to the chemical interaction with β-cyclodextrin via electrostatic and hydrogen bonds. The dipolar character of the zwitter-ionic structure improves the solubility and the dissolution rate of piroxicam and thus its rate of absorption (Bertoluzza et al *J Mol Struct* 1999, 480-481, 535).

Therefore, in order to ensure the best performances in terms of dissolution rate and absorption rate, so important for an analgesic action, the manufacturing process of PβCD should be able to achieve not only the completeness of the inclusion reaction but also the complete amorphization of the whole product. Moreover, since the dissolution profile is strictly dependent on the intramolecular structure assumed by piroxicam in the inclusion compound, the manufacturing process should be able to achieve the complete conversion of piroxicam in the zwitter-ionic form.

The amorphous PβCD inclusion compound in the 1:2.5 molar ratio and in which piroxicam is completely present in the zwitter-ionic form can be characterized by its Raman spectrum, X-ray powder diffraction pattern and thermal behavior.

The FT-Raman spectrum, obtained by simply packing the powder into a cup, is reported in FIG. 1. It shows the following main peaks in the 1650-1000 cm$^{-1}$ range (accuracy±1 cm$^{-1}$):

1613 cm$^{-1}$ (sh), 1593 (s), 1578 (sh), 1561 (w), 1525 (br), 1519 (br), 1464 (m), 1436 (m), 1394 (s), 1331 (brm)/1306 (sh), 1280 (w), 1260 (w), 1234 (w), 1217 (vw), 1186 (w), 1158 (m), 1119 (m), 1083 (w), 1053 (w), 1036 (w), 992 (w), 947 (brw).

Legend: sh=shoulder; s=strong; m=medium; w=weak; vw=very weak; br=broad

Figure 2:
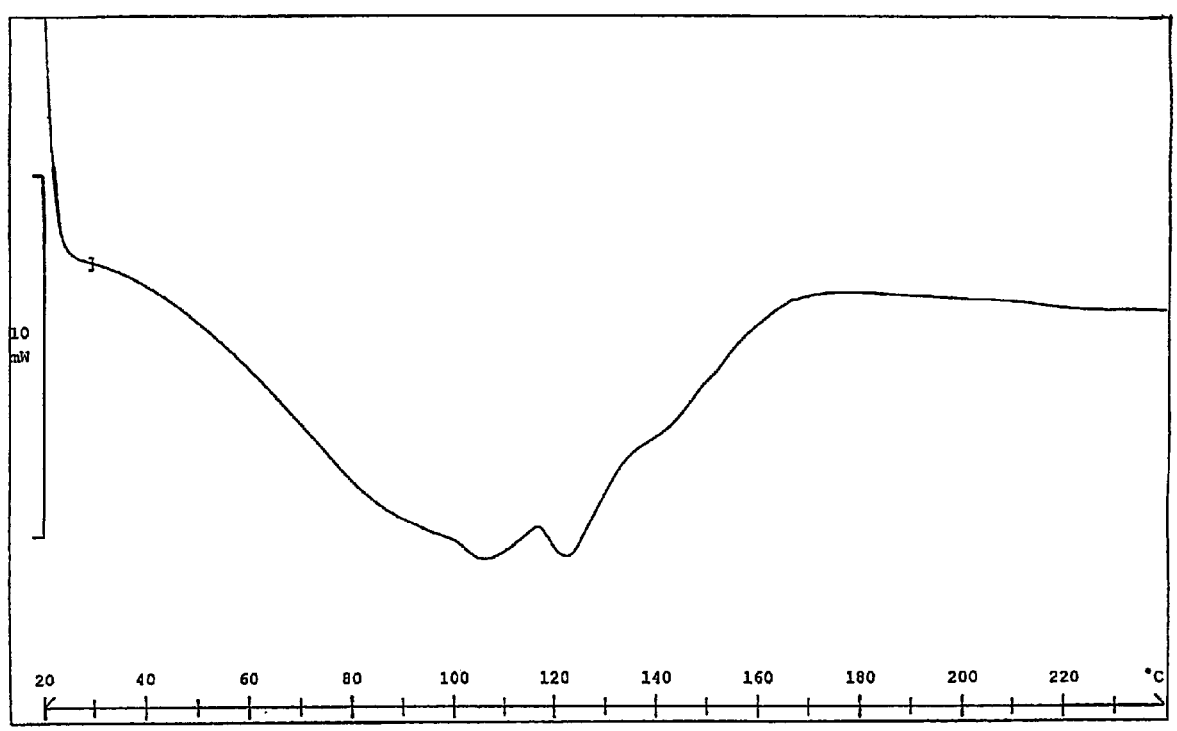

The thermal trace after differential scanning calorimetry (DSC) analysis does not show any endothermal melting peak at 190-200° C. typical of crystalline piroxicam. A typical DSC curve is shown in FIG. 2. The conditions are the following: starting temperature of 20° C.; scanning rate of 10° C./min; final temperature of 250° C.

In general terms, cyclodextrin inclusion complexes can be prepared on the basis of liquid state, solid state or semi-solid state reactions between the components. The first is accomplished by dissolving the cyclodextrin and the drug in a suitable solvent and subsequently isolating the solid state complex by crystallization, evaporation, spray-drying (Tokomura et al Yakuzaigaku 1985, 45, 1) and freeze-drying (Kurozumi et al Chem Pharm Bull 1975, 23, 3062).

In the semi-solid state, the two components are kneaded in the presence of small amounts of a suitable solvent, and the resulting complex is oven dried, screened and homogenized (Torricelli et al Int J Pharm 1991, 75, 147). In the solid state method, the two components may be optionally screened to uniform particle size and thoroughly mixed whereafter they are ground in a high-energy mill with optional heating, screened and homogenized.

Said methods have also been applied to the preparation of inclusion compounds constituted of piroxicam (P) and cyclodextrins (CDs).

For instance, EP 153998 discloses that complexes of P and CDs in a molar ratio comprised between 1:1 and 1:10 can be prepared in different ways:
a) by crystallization from an aqueous or an organic/aqueous solution containing the two ingredients;
b) by evaporation of a water/ammonia solution
c) by freeze-drying or atomization in air stream (spray drying) of a water/ammonia solution.

All the examples refer to preparations of 1:2.5 PβCD on a lab scale (from milligram to grams).

EP 449167 discloses a process for preparing P:CD complexes characterized in that the two ingredients, both in powder form, are mixed together, then co-ground in a high-energy mill whose grinding chamber has been saturated with steam.

Also in this case, the preparation of 1:2.5 PβCD showing the best performance was obtained on a gram scale.

In the example 2 of EP 449167, the dissolution rate of tablets containing as active ingredient the 1:2.5 PβCD prepared according to the claimed process was compared with that of analogous pharmaceutical composition containing the same active ingredient obtained by different methods and with a piroxicam composition in the form of capsules available on the market. The conditions of the dissolution test are not specified.

In this test, although the rate of dissolution of piroxicam from the inclusion complex obtained according to the method of the patent was the highest, ≧90% of dissolved piroxicam in ten min (600 ") was achieved from all the formulations, including the capsules.

The technical problem underlying the invention is to obtain good performances of the tablets prepared with the complex, in term of dissolution rate, when moving from lab to industrial scale.

According to the invention, on an industrial scale, 1:2.5 PβCD can be obtained by freeze-drying (lyophilization). Lyophilization is the process of removing water from a product by sublimation, i.e. at a product temperature that is lower than its eutectic temperature. This process is performed by means of a lyophilization equipment (freeze-dryer) which consists of a drying chamber with temperature-controlled shelves, a condenser to trap water removed from the product, a cooling system to supply refrigerant to the shelves and condenser and a vacuum system to reduce the pressure in the chamber and condenser to facilitate the drying process.

In the case of 1:2.5 PβCD, the lyophilisation process according to the invention comprises the following steps:
i. dissolving piroxicam and β-cyclodextrin in hot water in the presence of ammonium hydroxide;
ii. bringing the solution to a temperature of at least about −10° C. in order to achieve its complete freezing;
iii. further lowering the temperature of the frozen solution, i.e. to a temperature lower than the eutectic temperature of the product (−18° C.), i.e. at least −20° C. and preferably at between −30° C. and −40° C.;
iv. drying the frozen solution under vacuum.

It has been found and it is a first aspect of the present invention that in order to obtain 1:2.5 PβCD characterized by: i) completeness of the inclusion reaction; ii) complete amorphization; iii) complete conversion of piroxicam into the zwitter-ionic form, it is necessary to cool the solution to a temperature at which the complete freezing occurs as fast as possible and anyway at a rate equal to or higher than about 1° C./min.

A high cooling rate is necessary to 'freeze' and so maintain in the solid state the same structure of the inclusion complex in solution, with piroxicam in the zwitter-ionic form.

The inventors have indeed found that, if the cooling process is carried out at a lower rate, β-cyclodextrin begins to re-crystallize before the complete freezing of the solution followed by de-complexation of piroxicam and partial loss of the zwitter-ionic structure.

The rapid cooling of the solution can be performed partitioning the solution on trays that are placed on the temperature-controlled shelves of the freeze-dryer. In order to cool the solution at a rate equal to or higher than about 1° C./min, the temperature-controlled shelves should be pre-cooled at a temperature of at least −30° C., preferably −40° C.

In an alternative embodiment, in order to further speed-up the cooling process, the solution of the product can be frozen outside the freeze-dryer, for instance by pouring it in a dewar filled with liquid nitrogen, then submitting the resulting product, once recovered, to the drying process in the freeze-dryer.

In fact, it has been found and this is a further aspect of the invention, that, as a result of the freezing by liquid nitrogen, a product in the form of solid granules is formed. Solid granules, in turn, have an increased surface of sublimation than the powder in form of layers as obtained by cooling the solution on the temperature-controlled shelves, thus providing a reduction of the time of drying and an increase in the production yield.

None of the documents of the prior art, mention of the criticality of the cooling rate for obtaining freeze-dried PβCD in 1:2.5 molar ratio fulfilling the requirements outlined above, i.e.: i) completeness of the inclusion reaction; ii) complete amorphization; iii) complete conversion of piroxicam in the zwitter-ionic form. Nevertheless, there is mention of the advantages which can be achieved in term of productive yield by submitting the solution containing the complex to a pre-freezing treatment in liquid nitrogen.

Example 4 of EP 153998, referring to the preparation of PβCD by freeze-drying, states that the limpid solution was poured into a freeze-dryer, pre-cooled to −20° C. None is said about the importance of the cooling rate of the solution and the −20° C. temperature is not enough for guaranteeing a cooling rate of the hot solution equal to or higher than 1° C./min.

In Acerbi et al (Drug Invest 1990, 2, Suppl. 4, 29-36), a flow-chart showing the manufacturing process(es) for PβCD is sketched. As far as freeze-drying is concerned, only the temperature of the frozen solution before drying (−40° C.) is indicated.

Also in this case nothing is reported about the criticality of the conditions of the freezing step and in particular of the rate of cooling.

DETAILED DESCRIPTION OF THE INVENTION

The characteristics of the process of the invention for preparing PβCD inclusion compounds, will be more apparent from the following detailed description.

The process of the invention consists of lyophilization. Lyophilizers in a wide variety of sizes and configurations can be used. In a first step, piroxicam and β-cyclodextrin in a suitable molar ratio and ammonium hydroxide are added to a tank provided with a tap containing water brought to a temperature higher than 60° C., preferably higher than 70° C., more preferably between 70 and 75° C., then mixed until dissolution. In a second step the hot solution is poured through the tap on the temperature-controlled shelves pre-cooled at least at −30° C., in such a way as that the temperature of complete freezing (−10° C.) is achieved in not more than 90 min (rate≈1° C./min), preferably less than 60 min (rate≈1.5° C./min). More preferably, the shelves are pre-cooled to −40° C. in order to achieve the temperature of initial freezing (about −5° C.) in about 30 min. In a third step, the temperature is further lowered down to at least −20° C. and preferably to between −30° and −40° C., i.e. to a temperature lower than the eutectic temperature of the product (−18° C.), in about 120 min (overall time of freezing: 210 min). The frozen product is then submitted to the drying phase under vacuum by bringing the temperature of shelves at 50-60° C., preferably at 55° C. The drying phase may be carried out in one or two steps and the product may be submitted to a secondary drying bringing the temperature of the shelves at the same temperature of 50-60° C. in order to further reduce the content of residual water of the complex.

Alternatively, the hot solution is poured through the tap into a dewar filled with liquid nitrogen in such a way that a temperature lower than the eutectic temperature (−18° C.) is achieved almost instantaneously (rate much higher than 1° C./min).

The frozen product is recovered and submitted to the drying phase on the shelves of a freeze-dryer as described above.

According to the invention, piroxicam and β-cyclodextrin are used in a 1:1 and 1:4 molar ratio, preferably 1:2.5.

In the first step of the process concentrated ammonium hydroxide is advantageously used, preferably in a conc. of 28-30% w/w and in a 1:1 ratio w/w with respect to piroxicam.

The PβCD complex obtained with the process of the invention can be advantageously used to prepare pharmaceutical compositions having analgesic, anti-inflammatory and anti-rheumatic activity, for the oral, rectal and topical administration, preferably in the form of tablets, effervescent tablets or sachets for oral administration.

Advantageously the tablets for oral administration contain between 40 mg and 200 mg of the 1:2.5 complex per unit dose, preferably 95.6 mg or 191.2 mg (respectively corresponding to 10 and 20 mg of piroxicam) and lactose, crospovidone, sodium starch glycolate, silica, starch and magnesium stearate as excipients.

The following examples better illustrate the invention.

EXAMPLE 1

Preparation of 1:2.5 PβCD by Lyophilisation

About 50 liters of water was poured into a tank and heated up to a temperature of 70-73° C. 8.6 kg (7.57 moles) of β-cyclodextrin, 1 kg (3.02 moles) of piroxicam and 1 kg of 28% ammonium hydroxide were added in succession, and the mixture stirred for 30 min. The solution was poured through the tap on the temperature-controlled shelves of the freeze-dryer pre-cooled at −40° C. After 210 min, the frozen product reaches the temperature of −30° C., so it is first submitted to a primary drying phase under vacuum by bringing the temperature of shelves at 50-60° C., then to a secondary drying phase at the same temperature for reducing the content of residual water.

The 1:2.5 PβCD product in the form of layers is collected from the trays.

The resulting product shows the Raman spectrum and the thermal curve reported respectively in FIGS. 1 and 2. Powder X-ray analysis shows the diffused diffraction pattern typical of amorphous products.

EXAMPLE 2

Dissolution Rate of the Tablets

Tablets, containing 1:2.5 PβCD as active ingredient prepared according to the method of Example 1, were prepared by direct compression according to the following unit of composition:

| Ingredient | Quantity (mg/tablet) |
|---|---|
| 1:2.5 PβCD | 191.2 |
| Lactose monohydrate | 102.8 |
| Crospovidone | 50 |
| Sodium starch glycolate | 20 |
| Colloidal hydrated silica | 20 |
| Pregelatinized starch | 10 |
| Magnesium stearate | 6 |
| Total | 400 |

It is well known that the parameters used for performing the dissolution test are very critical and can strongly affect the dissolution performances. For discriminating among the various inclusion complexes, the dissolution test was performed according to the USP paddle method with the following modifications: six tablets were dissolved in 300 ml water at 37° C. and at 125 r.p.m; an aliquot was withdrawn after 10 min and the content of piroxicam was determined by spectrophotometric analysis.

In order to obtain the desired absorption profile, the dissolution specification requires an amount of dissolved piroxicam ≧90% in ten minutes.

The tablets containing the 1:2.5 PβCD complex obtained according to the process of the present invention (Example 1) fulfil such a specification, while those containing the same complex prepared according to the processes of the prior art do not.

The invention claimed is:

1. A process of lyophilization for the preparation of a piroxicam:β-cyclodextrin inclusion compound in a 1:2.5 molar ratio conducted on a kilogram scale, comprising:
    (a) dissolving piroxicam and β-cyclodextrin in the molar ratio of 1 to 2.5 and ammonium hydroxide in water brought to a temperature of at least 60° C.;
    (b) pouring the piroxicam and β-cyclodextrin dissolved in water from (a) on temperature-controlled shelves of a freeze-dryer pre-cooled to a temperature of at least −30° C. to lower the temperature of the solution to −10° C. at a cooling rate equal to or higher than 1° C./min, to produce a frozen solution;
    (c) further lowering the temperature of the frozen solution to at least −20° C.; and
    (d) drying the frozen solution under vacuum,
    wherein the inclusion reaction is complete with complete amorphization of the inclusion compound and complete conversion of the piroxicam to the zwitter-ionic form.

2. The process of claim 1, wherein the cooling rate is 1.5° C./min.

3. The process of claim 1, wherein the shelves of the freeze-dryer are pre-cooled to a temperature of at least −40° C.

4. The process of claim 1, wherein the temperature is lowered to between −30 and −40° C.

5. The process of claim 1, wherein the water brought to a temperature of at least 60° C. from (a) is poured in a dewar filled with liquid nitrogen.

6. The process of claim 5, wherein the product obtained is in the form of solid granules.

7. The process of claim 1, wherein (d) is carried out at a temperature of 50-60° C.

8. The process of claim 1, wherein the water in (a) is brought to a temperature of at least 70° C.

9. The process of claim 8, wherein the water is brought to a temperature between 70 and 75° C.

10. The process of claim 1, wherein the ammonium hydroxide is used in a concentration of 28-30% and in a 1:1 ratio (w/w) with respect to piroxicam.

11. The process of claim 1, wherein the temperature of complete freezing of the hot solution is achieved in not more than 90 minutes.

12. The process of claim 1, which is conducted on an industrial scale.

* * * * *